United States Patent [19]

Kühle et al.

[11] 4,402,980
[45] Sep. 6, 1983

[54] SULPHONIC ACID CYCLOALKYLAMIDES AND THEIR USE AS MICROBICIDES

[75] Inventors: Engelbert Kühle, Bergisch-Gladbach; Wilfried Paulus; Hermann Genth, both of Krefeld; Erich Klauke, Odenthal, all of Fed. Rep. of Germany

[73] Assignee: Bayer Aktiengesellschaft, Leverkusen, Fed. Rep. of Germany

[21] Appl. No.: 195,023

[22] Filed: Oct. 8, 1980

[30] Foreign Application Priority Data

Oct. 23, 1979 [DE] Fed. Rep. of Germany ....... 2942677

[51] Int. Cl.³ ..................... A01N 9/16; C07C 143/72; C07C 143/84
[52] U.S. Cl. ..................... 424/321; 564/79; 564/96; 564/98; 260/453 RW
[58] Field of Search .............. 564/79, 96, 98; 260/453 RW; 424/321

[56] References Cited

U.S. PATENT DOCUMENTS

| | | | |
|---|---|---|---|
| 2,779,788 | 1/1957 | Gysin et al. | 564/97 |
| 2,779,941 | 1/1957 | Gysin et al. | 564/99 |
| 2,844,628 | 7/1958 | Kuhle et al. | 564/79 |
| 3,285,929 | 11/1966 | Klauke et al. | 564/79 X |
| 3,678,017 | 7/1972 | Shelton et al. | 564/98 X |
| 3,703,500 | 11/1972 | Nast et al. | 564/79 X |
| 4,068,000 | 1/1978 | Edwards | 424/321 |
| 4,107,332 | 8/1978 | Chan et al. | 424/321 |
| 4,208,348 | 6/1980 | Chan et al. | 564/98 X |
| 4,295,874 | 10/1981 | Edwards | 564/96 X |

FOREIGN PATENT DOCUMENTS 2551504  5/1977  Fed. Rep. of Germany ........ 564/98

*Primary Examiner*—Thomas A. Waltz
*Attorney, Agent, or Firm*—Sprung, Horn, Kramer & Woods

[57] ABSTRACT

A N-sulphenylated sulphonic acid cyclohexylamide of the formula

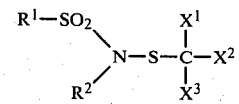

wherein
$R^1$ denotes lower alkyl, chloroalkyl or dialkylamino,
$R^2$ denotes a cycloalkyl radical which is optionally substituted by lower alkyl and
$X^1$, $X^2$ and $X^3$ are identical or different and represent fluorine or chlorine, a process for its preparation, and its use as a microbicidal agent including a microbicidal agent containing the same.

8 Claims, No Drawings

SULPHONIC ACID CYCLOALKYLAMIDES AND THEIR USE AS MICROBICIDES

The invention relates to new sulphonic acid cycloalkylamides, a process for their preparation and their use as microbicides.

To protect industrial materials, such as, for example, wood, it is in general not possible to incorporate a solid active compound into the material. It is therefore customary to convert the active compound into a formulation with a solvent and thus to incorporate it into the material (Chemie der Pflanzenschutz- und Schädlingsbekämpfungsmittel (Chemistry of Plant Protection Agents and Agents for Combating Pests), Volume 4, pages 257 to 272, Springer Verlag 1977).

The action of N,N-dimethyl-N-phenyl-N-(fluorodichloromethylthio)-sulphamide against fungi which are harmful to wood is described in "Holz als Roh- und Werkstoff" 35, 233-237 (1977). However, this compound has a very low solubility in the solvents and formulating agents customary for agents for the protection of wood, so that large amounts of solvent are necessary for the required amount of active compound to be applied to and/or incorporated into the wood.

This problem is solved, inter alia, with the aid of the new N-sulphenylated sulphonic acid cycloalkylamides according to the invention.

New N-sulphenylated sulphonic acid cycloalkylamides of the formula

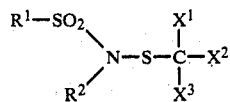

wherein
R$^1$ denotes lower alkyl, chloroalkyl or dialkylamino,
R$^2$ denotes a cycloalkyl radical which is optionally substituted by lower alkyl and
X$^1$, X$^2$ and X$^3$ are identical or different and represent fluorine or chlorine, have been found.

Lower alkyl radicals (R$^1$) can be straight-chain or branched aliphatic hydrocarbon radicals with 1 to about 6 carbon atoms. Preferred lower alkyl radicals are the methyl radical and the ethyl radical. The following lower alkyl radicals may be mentioned as examples: methyl, ethyl, propyl, isopropyl, butyl, isobutyl, pentyl, isopentyl, hexyl and isohexyl.

Chloroalkyl radicals (R$^1$) which may be mentioned are essentially the lower alkyl radicals (R$^1$) in which hydrogen atoms are replaced by one or more chlorine atoms. Preferred chloroalkyl radicals contain 1 to 3 chlorine atoms, preferably 1 chlorine atom.

Dialkylamino radicals (R$^1$) are in general amino groups carrying two optionally different lower alkyl radicals (R$^1$). Preferred dialkylamino radicals are the dimethylamino radical and the diethylamino radical.

Cycloalkyl radicals (R$^2$) which may be mentioned are essentially the cyclopentyl and the cyclohexyl radical. The cyclohexyl radical is particularly preferred. The cycloalkyl radicals can carry one or more lower alkyl radicals (R$^1$) as substituents. Preferred cycloalkyl radicals carrying lower alkyl groups contain 1 to 4 lower alkyl groups, preferably methyl groups or ethyl groups.

Compounds of the formula

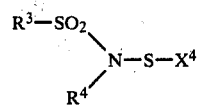

wherein
R$^3$ denotes methyl, ethyl, chloromethyl, chloroethyl, dimethylamino or diethylamino,
R$^4$ denotes a cyclopentyl or cyclohexyl radical which is optionally substituted by 1 to 4 methyl or ethyl radicals and
X$^4$ denotes dichlorofluoromethyl, are preferred N-sulphenylated sulphonic acid cycloalkylamides according to the invention.

The following new N-sulphenylated sulphonic acid cycloalkylamides may be mentioned specifically: the N-dichlorofluoromethylsulphenyl derivatives of methane-, ehtane- and butane-sulphonic acid cyclohexylamide, of chloromethanesulphonic acid cyclohexylamide, or dimethylaminosulphonic acid cyclohexylamide, of methanesulphonic acid cyclopentylamide and of methanesulphonic acid 3,5,5-trimethylcyclohexylamide, and the N-trichloromethylsulphenyl derivatives of methane- and chloromethanesulphonic acid cyclohexylamide.

In addition, a process has been found for the preparation of N-sulphenylated sulphonic acid cycloalkylamides, which is characterised in that sulphonic acid cycloalkylamides of the formula

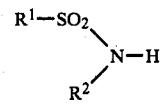

wherein
R$^1$ and R$^2$ have the abovementioned meaning, are reacted with a sulphenyl chloride of the formula

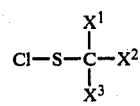

wherein
X$^1$, X$^2$ and X$^3$ have the abovementioned meaning, in the presence of a diluent and in the presence of an acid-binding agent.

The process according to the invention can be illustrated with the aid of the following equation:

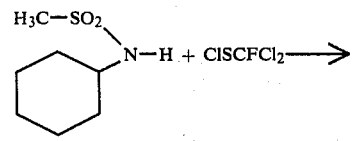

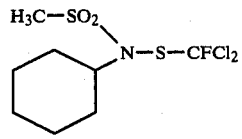

Sulphonic acid cycloalkylamides for the process according to the invention can be prepared from the corresponding sulphonic acid chlorides and primary cycloalkylamines by methods which are in themselves known (Houben-Weyl, 4th edition, Volume 9, page 398). Examples which may be mentioned are: methane-, ethane- and butane-sulphonic acid cyclohexylamide, methane- sulphonic acid cyclopentylamide, methanesulphonic acid 4-methylcyclohexylamide, methanesulphonic acid 3,5,5-trimethylcyclohexylamide, chloromethanesulphonic acid cyclohexylamide, 2-cyclopentanesulphonic acid cyclohexylamide and dimethylaminocyclohexylamide.

Sulphenyl chlorides for the process according to the invention are known (Houben-Weyl, 4th edition, Volume 9, page 787, and Angew. Chem. 76 807 (1964)).

The following sulphenyl chlorides may be mentioned as examples for the process according to the invention: trichloromethanesulphenyl chloride and dichlorofluoromethanesulphenyl chloride.

Possible diluents for the process according to the invention are inert organic solvents. These include ethers, such as diethyl ether and dioxane, hydrocarbons, such as toluene, and chlorinated hydrocarbons, such as chloroform and chlorobenzene. However, it is also possible to carry out the reaction in an aqueous medium.

An acid-binding agent is added in the process according to the invention in order to bond the hydrogen chloride formed during the reaction. A tertiary amine, such as a tertiary lower alkyl amine, e.g. triethylamine, or inorganic bases, such as alkali metal hydroxydes (NaOH or KOH) or carbonates ($Na_2CO_3$) are preferably used.

The process according to the invention is in general carried out in the temperature range from 0° to 100° C., preferably from 20° to 50° C.

The preparation of the new N-sulphenylated sulphonic acid cycloalkylamides by the process according to the invention is in general effected by bringing together the starting components. After the reaction, the mixture is washed, if appropriate, with water and the organic phase, which contains the reaction product, is separated off. Crystalline N-sulphenylated sulphonic acid cycloalkylamides are obtained from the organic phase.

The new N-sulphenylated sulphonic acid cycloalkylamides according to the invention are compounds with a particularly powerful microbicidal action. They can be used, for example, for protecting industrial materials against microbial degradation or against a change in the industrial materials caused by microorganisms. Examples of industrial materials are adhesives, sizes, paper and cardboard, textiles, leather, wood, paints, plaster and materials which are stored in containers and can be damaged or destroyed by microbial action. The active compounds according to the invention are particularly suitable for the protection of wood.

Their good solubility in the solvents customary in the field of protection of wood, such as, for example, petroleum fractions and benzine (gasoline) fractions, such as white spirit (low-boiling hydrocarbon fraction), and furthermore in solubilizing agents, such as ethyl acetate and xylene, is noteworthy and surprising. Mixtures of aromatic hydrocarbons (boiling point 150° to 180° C.) and benzine (gasoline) fractions (boiling point 140° to 200° C.) are the preferred solvents.

Examples of micro-organisms which can cause industrial materials to be degraded or changed are bacteria, fungi and algae.

Examples of bacteria and fungi which may be mentioned are: *Escherichia coli, Staphylococcus aureus, Pencicillium glaucum, Chaetomium globosum, Aspergillus niger, Coniophora cerebella, Cladosporium herbarum, Alternaria tenuis* and *Pullularia pullulans.*

The new N-sulphenylated sulphonic acid cycloalkylamides according to the invention have a particularly powerful fungicidal action.

The new N-sulphenylated sulphonic acid cycloalkylamides according to the invention can be converted to the customary formulations, such as solutions, emulsions, suspensions, powders, pastes and granules, depending on their field of application. These formulations can be produced in a manner which is in itself known, for example by mixing the active compounds with an extender, which can consist of a liquid solvent and/or of solid carriers, surface-active agents, such as emulsifiers and/or dispersing agents, being used if appropriate. Where water is used as an extender, organic solvents can, if appropriate, be used as auxiliary solvents.

The new active compounds according to the invention can be present in the formulations as a mixture with other known active compounds. The following active compounds may be mentioned as examples: benzimidazolyl-alkylcarbamate, tetramethyl-thiuram-disulphide, N-fluorodichloromethylthio-phthalimide and N,N-dimethyl-N'-phenyl-(N'-fluorodichloromethylthio)sulphamide.

The concentrations in which the microbicides according to the invention are used depend on the nature of the micro-organisms to be combated and on the extent to which they occur, and on the composition of the material to be protected. The optimum amount to be used can be established by a series of tests. In general, the concentrations used are in the range from 0.05 to 5% by weight, preferably 0.5 to 3% by weight, relative to the material to be protected. They can be employed in the form of a solution in which they are present in an amount of between 5 and 50 weight percent.

PREPARATION EXAMPLES

Example 1

$CH_3SO_2NSCFCl_2$

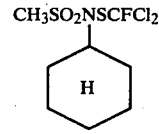

106 g (0.6 mol) of methanesulphonic acid cyclohexylamide and 102 g (0.6 mol) of dichlorofluoromethanesulphenyl chloride are dissolved in 500 ml of toluene, and 68 g of triethylamine are added dropwise at room temperature. The temperature rises to about 40° C. The reaction solution is extracted by shaking with water, the toluene solution is dried and the toluene is distilled off. 165 g (88% of theory) of the N-dichlorofluoromethylsulphenyl derivative of methanesulphonic acid cyclohexylamide, melting point 60° to 64° C., are obtained.

The following compounds are obtained in a similar manner:

Examples 2 to 9

$$A-SO_2N-SCFCl_2$$
$$|$$
$$B$$

(A and B are the substituents listed below)

| Example No. | A | B | | |
|---|---|---|---|---|
| 2 | ClCH$_2$ | cyclohexyl | melting point | 102° C. |
| 3 | (CH$_3$)$_2$N | cyclohexyl | melting point | 70–71° C. |
| 4 | CH$_3$— | 4-methylcyclohexyl | melting point | 47–48° C. |
| 5 | ClCH$_2$— | 4-methylcyclohexyl | $n_D^{20}$ | 1.5230 |
| 6 | (CH$_3$)$_2$N— | 4-methylcyclohexyl | melting point | 80–85° C. |
| 7 | CH$_3$— | 3,5,5-trimethylcyclohexyl | $n_D^{20}$ | 1.5056 |
| 8 | ClCH$_2$— | 3,5,5-trimethylcyclohexyl | $n_D^{20}$ | 1.5138 |
| 9 | (CH$_3$)$_2$N— | 3,5,5-trimethylcyclohexyl | $n_D^{20}$ | 1.5005 |

From Examples 10 and 11 which follow, it can be seen that compared with N,N-dimethyl-N'(fluorodichloromethylthio)sulphamide, which is already known, the substances according to the invention are both more readily soluble and more effective. Their application thus requires both less solvent and small amounts of active compound, which is of advantage, in particular, with regard to pollution of the environment.

Example 10

Solubility, in % by weight, of the active compound according to Example 1, 3, 4 and 6 in organic solvents [(N,N-dimethyl-N'-phenyl-N'(fluorodichloromethylthio)sulphamide is used for comparison].

| Solvent | Active compound according to Example | | | | N,N—dimethyl-N'—phenyl-N'—(fluorodichloromethylthio)-sulphamide |
|---|---|---|---|---|---|
| | 1 | 3 | 4 | 6 | |
| ethyl acetate | 67 | 48 | 77 | 29 | 11.7 |
| methylglycol acetate | 63 | 29 | 71 | 19 | 9.5 |
| white spirit aromatics | 10 | 8.3 | 7.5 | 7.5 | 1.2 |
| (boiling point 163–180° C.) | 56 | 36 | 40 | 24 | 7.5 |
| isomeric tetramethylbenzenes | 53 | 40 | 79 | 26 | |

The temperature of the subject was 20° C.

EXAMPLE 11

To demonstrate the activity against fungi, the minimum inhibitory concentrations (MIC) of active compounds according to the invention are determined:

Active compounds according to the invention are added, in concentrations of 0.5 mg/l to 5,000 mg/l, to an agar prepared from beer wort and peptone. After the agar has solidified, it is contaminated with pure cultures of the test organisms listed in the table. After storage at 28° C. and 60 to 70% relative atmospheric humidity for two weeks, the MIC is determined. The MIC is the lowest concentration of active compound at which no growth at all of the species of microbe used takes place, and is indicated in the table below. Data for the MIC values in mg/l for the action of the active compounds indicated below on fungi [comparison substance: N,N-dimethyl-N'-(fluorodichloromethylthio)sulphamide].

TABLE

| Test organism | Active compound according to Example: | | | | | | | | | N,N—Dimethyl-N'-phenyl N'(fluorodichloromethylthio)sulphamide (comparison) |
|---|---|---|---|---|---|---|---|---|---|---|
| | 1 | 2 | 3 | 4 | 5 | 6 | 7 | 8 | 9 | |
| *Penic. glaucum* | 10 | 10 | 350 | 10 | 10 | — | 500 | 20 | 500 | 35 |
| *Chaet. globosum* | 1.5 | 10 | 0.5 | 0.5 | 10 | 3.5 | 1.5 | 10 | 7.5 | 20 |
| *Asperg. niger* | 7.5 | 15 | 10 | 5 | 15 | 100 | 35 | — | 750 | 50 |
| *Conioph. cereb.* | 0.5 | 0.5 | 0.5 | 0.5 | 0.5 | 0.5 | 0.5 | 0.5 | 0.5 | 10 |
| *Cladosp. herb.* | 1.5 | 5 | 5 | 0.5 | 5 | 3.5 | 0.5 | 7.5 | 15 | 20 |
| *Altern. tenuis* | 0.5 | 5 | 1 | 0.5 | 7.5 | 0.5 | 0.5 | 10 | 20 | 20 |
| *Pull. pullulans* | 0.5 | 5 | 7.5 | 0.5 | 5 | 5 | 5 | 10 | 350 | 20 |

What is claimed is:

1. A N-sulphenylated sulphonic acid cycloalkyl amide of the formula

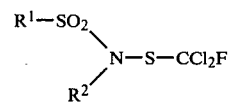

wherein
R$^1$ denotes lower alkyl, chloroalkyl or dialkylamino and
R$^2$ denotes a cycloalkyl radical which is optionally substituted by lower alkyl.

2. A N-sulphenylated sulphonic acid cycloalkyl amide according to claim 1 of the formula

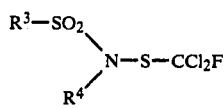

wherein

R³ represents methyl, ethyl, chloromethyl, chloroethyl, dimethylamino or diethylamino and R⁴ denotes a cyclopentyl or cyclohexyl radical which is optionally substituted by 1-4 methyl or ethyl radicals 3. A compound according to claim 1, having the formula

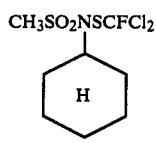

4. A microbidical agent comprising a compound of the formula

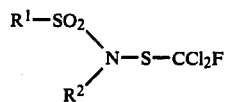

wherein

R¹ denotes lower alkyl, chloroalkyl or dialkyl amino and

R² denotes a cycloalkyl radical which is optionally substituted by lower alkyl and a diluent.

5. A microbicidal agent according to claim 4, wherein said compound has the formula

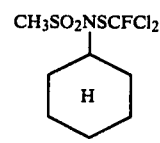

6. A microbicidal agent according to claim 4 wherein said diluent is a solvent.

7. A microbicidal agent according to claim 6 wherein said solvent is a petroleum solvent.

8. A microbicidal agent according to claim 6 wherein said solvent is white spirit, a gasoline fraction of boiling point 140°–200° C., xylene, ethyl acetate, a mixture of aromatic hydrocarbon of boiling point 150° to 180° C. or ethyl acetate.

* * * * *